(12) United States Patent
Tamura

(10) Patent No.: US 8,579,821 B1
(45) Date of Patent: *Nov. 12, 2013

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

( * ) Notice: Subject to any disclaimer, the term of this patent is extended or adjusted under 35 U.S.C. 154(b) by 1008 days.

This patent is subject to a terminal disclaimer.

(21) Appl. No.: 12/633,105

(22) Filed: Dec. 8, 2009

Related U.S. Application Data

(60) Provisional application No. 61/159,187, filed on Mar. 11, 2009.

(51) Int. Cl.
*A61B 8/00* (2006.01)
(52) U.S. Cl.
USPC ............................ 600/455; 600/437; 600/453
(58) Field of Classification Search
USPC .......................................... 600/407, 437–472
See application file for complete search history.

(56) References Cited

U.S. PATENT DOCUMENTS 8,366,624 B1 * 2/2013 Tamura .......................... 600/455

* cited by examiner

*Primary Examiner* — Tse Chen
*Assistant Examiner* — Mark Remaly
(74) *Attorney, Agent, or Firm* — Buckley, Maschoff & Talwalkar LLC

(57) ABSTRACT

Systems are described to acquire color Doppler data associated with a pulse repetition frequency ($f_{PRF}$), detect a first area of the color Doppler data representing a zero color Doppler value, detect a second area of the color Doppler data adjacent to the first area and representing non-zero color Doppler values in a first direction, detect a first transition between the second area and a third area of the color Doppler data adjacent to the second area and representing non-zero color Doppler values in a second direction opposite the first direction, determine that the absolute difference between color Doppler values of the second area and the third area at the first transition is more than a preset value, subtract, in response to the determination, a color Doppler value corresponding to a Doppler shift frequency of $f_{PRF}$ from each of the color Doppler values of the third area if the second direction is positive, and add, in response to the determination, the color Doppler value corresponding to a Doppler shift frequency of $f_{PRF}$ to each of the color Doppler values of the third area if the second direction is negative.

25 Claims, 12 Drawing Sheets

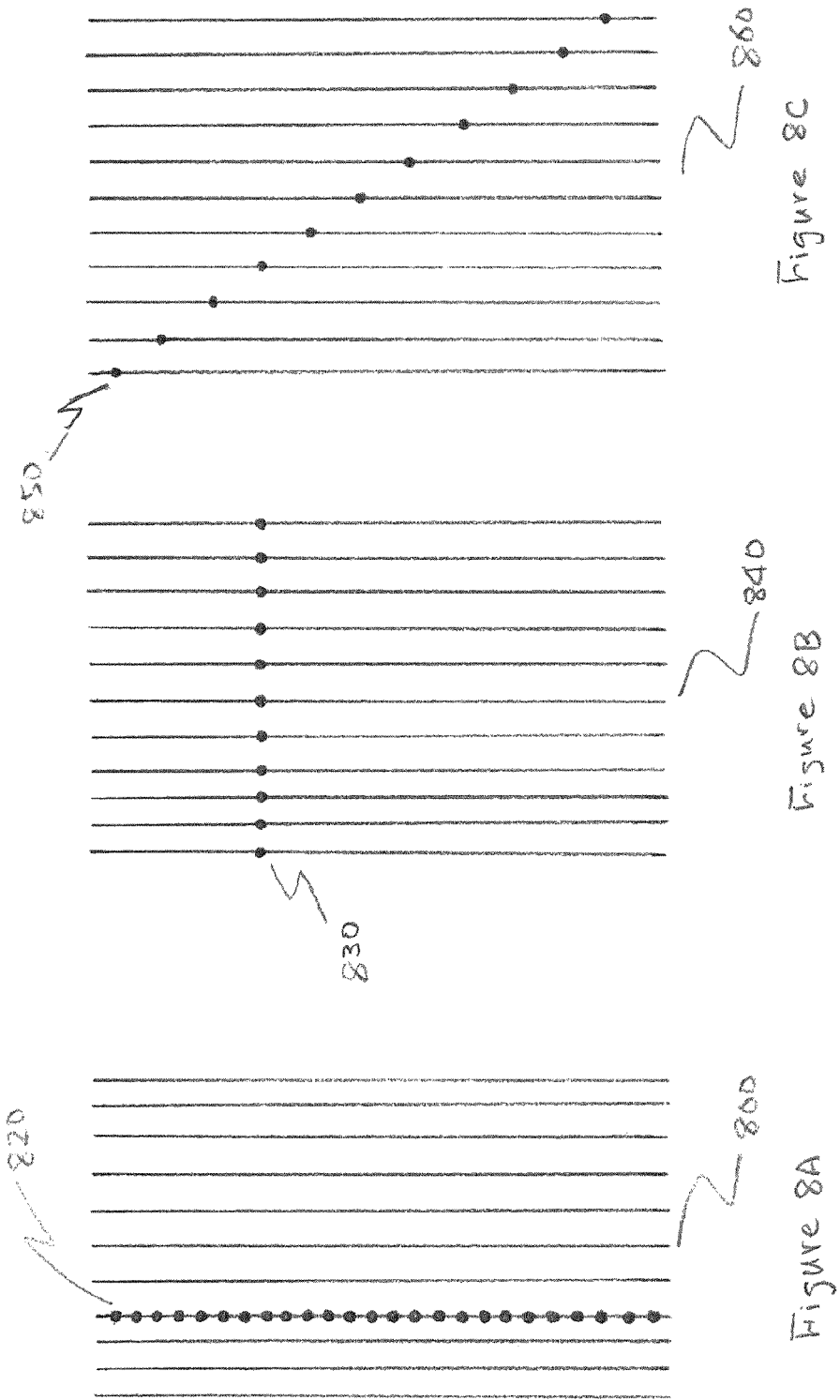

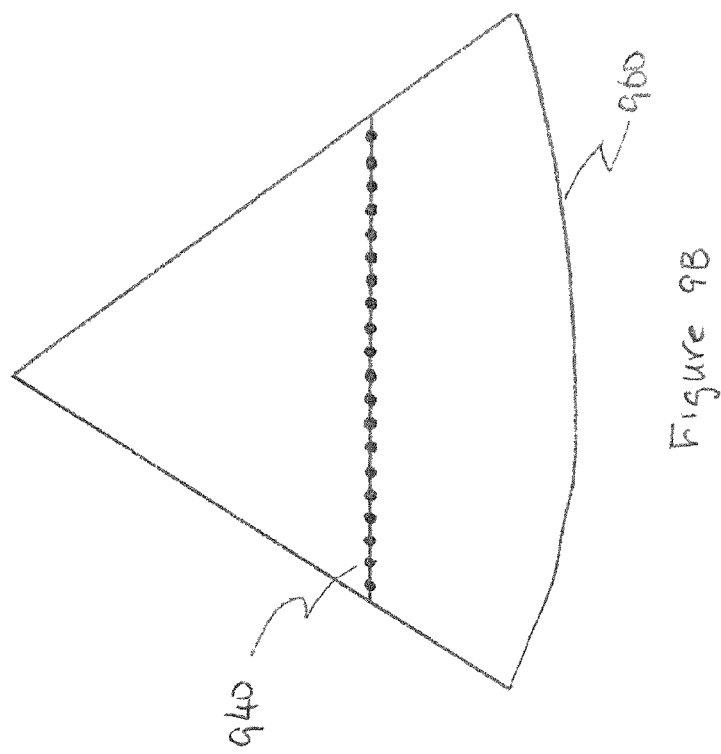
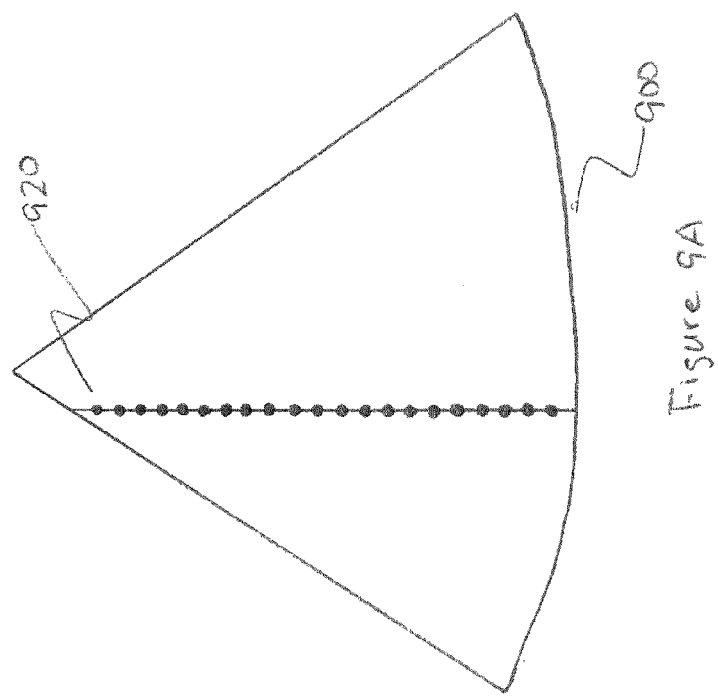

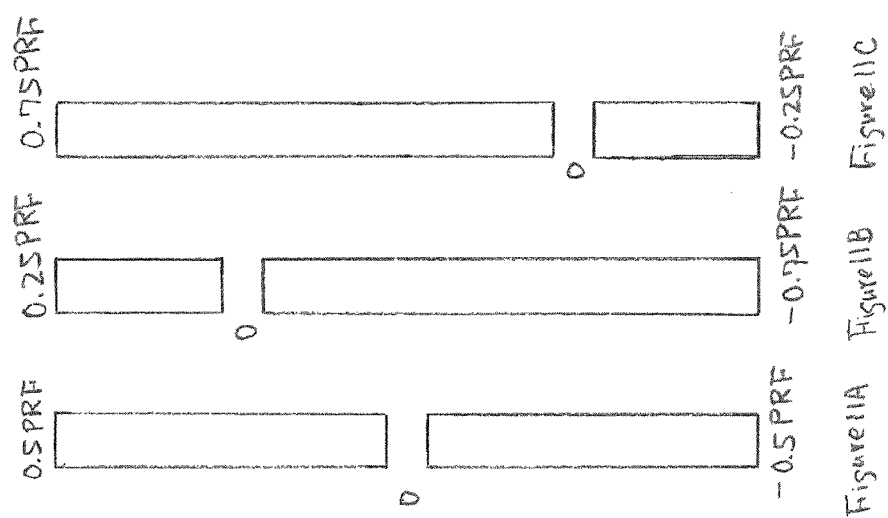

METHODS AND APPARATUS FOR ULTRASOUND IMAGING

CROSS-REFERENCE TO RELATED APPLICATION

The present application claims priority to U.S. Provisional Patent Application Ser. No. 61/159,187, filed on Mar. 11, 2009 and entitled "Method and Apparatus for Ultrasound Imaging", the contents of which are incorporated herein by reference for all purposes.

BACKGROUND

Systems and methods described herein generally relate to the field of ultrasound imaging. More specifically, embodiments described below relate to methods and systems for color flow imaging.

Ultrasound is used to image various internal structures, including but not limited to the heart, the liver, a fetus, and blood vessels. For diagnosis of cardiovascular diseases, color Doppler (or color flow) imaging is usually used to visualize blood flow in the heart or blood vessels. Abnormal conditions often increase blood flow velocity in comparison to that under normal conditions. The increased velocity may result in aliasing within a corresponding color Doppler image. Color Doppler uses a pulse ultrasound technology for its spatial sampling capability, which limits the maximum frequency which can be detected without experiencing aliasing. The pulse repetition frequency (PRF), which is also the sampling frequency, sets the maximum frequency limitation. This limitation, in turn, limits the maximum blood flow velocity which can be measured without exhibiting aliasing. In cardiac cases especially, the limitation is severe because the imaging depth is usually deep and thus PRF cannot be set high enough to measure abnormally high blood velocities, for example, regurgitation jets across heart valves. Therefore, in abnormal cardiac conditions, color Doppler often exhibits aliasing, thereby reducing the reliability of any diagnosis based on the blood flow image. Thus, there exists a need to overcome this aliasing problem.

SUMMARY

Methods and systems are described to acquire color Doppler data associated with a pulse repetition frequency ($f_{PRF}$), detect a first area of the color Doppler data representing a zero color Doppler value, detect a second area of the color Doppler data adjacent to the first area and representing non-zero color Doppler values in a first direction, detect a first transition between the second area and a third area of the color Doppler data adjacent to the second area and representing non-zero color Doppler values in a second direction opposite the first direction, determine that the absolute difference between color Doppler values of the second area and the third area at the first transition is more than a preset value, subtract, in response to the determination, a color Doppler value corresponding to a Doppler shift frequency of $f_{PRF}$ from each of the color Doppler values of the third area if the second direction is positive, and add, in response to the determination, the color Doppler value corresponding to a Doppler shift frequency of $f_{PRF}$ to each of the color Doppler values of the third area if the second direction is negative

BRIEF DESCRIPTION OF THE DRAWINGS

FIG. 8A: Aliasing detection in a vertical direction using color flow lines.
FIG. 8B: Aliasing detection in horizontal direction using color flow lines.
FIG. 8C: Aliasing detection in a diagonal direction using color flow lines.
FIG. 9A: Aliasing detection in vertical direction using a color flow image.
FIG. 9B: Aliasing detection in horizontal direction using a color flow image.
FIG. 11A: Color-coded Doppler shift frequency (velocity) scale with no baseline shift.
FIG. 11B: Color-coded Doppler shift frequency (velocity) scale with a baseline shift of $$\frac{f_{PRF}}{4}.$$

FIG. 11C: Color-coded Doppler shift frequency (velocity) scale with a baseline shift of $$-\frac{f_{PRF}}{4}.$$

DETAILED DESCRIPTION

Figure 1:
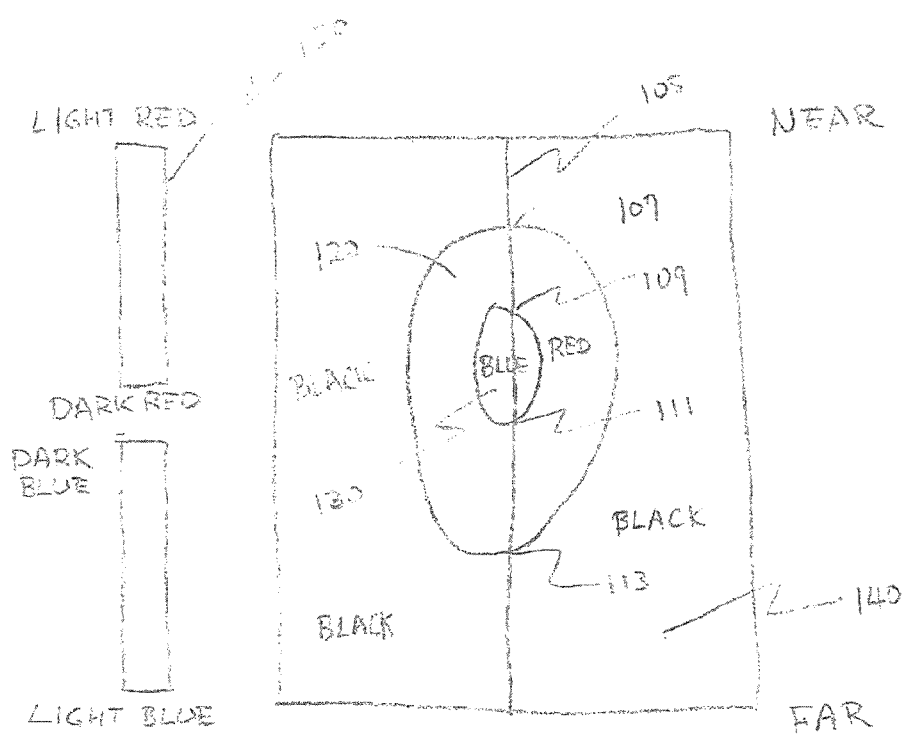
FIG. 1: Aliased color Doppler flow line data.

Embodiments will be described with reference to the accompanying drawing figures wherein like numbers represent like elements throughout. Before embodiments of the invention are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

It should be noted that embodiments are not limited to any particular software language described or that is implied in the figures. One of ordinary skill in the art will understand that a variety of alternative software languages may be used for implementation of some embodiments. It should also be understood that some of the components and items are illustrated and described as if they were hardware elements, as is common practice within the art. However, one of ordinary skill in the art, and based on a reading of this detailed description, would understand that, in at least one embodiment, components in the method and system may be implemented in software or hardware.

Ultrasound is transmitted by an ultrasound transducer into a human body to image various internal structures, including but not limited to blood vessels, a fetus, and the heart. Scatterers in tissue scatter the ultrasound and the scattered ultrasound is returned to the transducer. A receive beamformer creates ultrasound beams from the scattered ultrasound and a post processor creates a B-mode image of tissues based on the amplitude of the ultrasound beams.

Blood vessels or the heart are often imaged, since they indicate cardiovascular conditions of patients. Blood flow information is usually acquired using color Doppler and spectral Doppler techniques.

Color Doppler is a two-dimensional imaging technique commonly used for imaging blood flow by sending ultrasonic waves into the blood flow and detecting the scattered ultrasound from the moving red cells. It consists of many beams similar to B-mode image. In order to detect flow velocity, color Doppler transmits ultrasound signals several times per position to detect motion. To create a two-dimensional flow image, the transmit position is shifted by sub-millimeters, or about the order of an ultrasound wavelength. The transmit position shifting is repeated about 100 times to cover several centimeters and to create a two-dimensional flow image in linear and convex formats. For a phased array transducer or a sector image format, the transmit direction is changed a small angle, for example, about 0.5-1.0 degrees. This is repeated approximately 100 times to cover about 90 degrees of a sector image. For each transmit position or direction, ultrasound is transmitted several times. Received beamformed RF ultrasound signals undergo quadrature demodulation resulting in complex, Doppler I-Q signals.

In a color Doppler technique, the ultrasound is transmitted at a pulse repetition frequency (PRF) and the blood flow velocity is detected as the shift in frequency (Doppler shift frequency) in the received ultrasound signal. The received ultrasound is mixed with in-phase (0 degrees) and quadrature (90 degrees) reference signals of the same frequency as the transmit ultrasound frequency. After low-pass filtering high frequency components (i.e. second harmonics), only the baseband signals are obtained. Wall-filtering (e.g. highpass filtering) is applied to the baseband signals to remove strong clutter noise from tissue and slowly moving tissues such as blood vessel walls, resulting in complex I-Q Doppler signals. The wall filtering is performed because the Doppler I-Q signals may contain blood flow signal components as well as stationary tissue signal components. The stationary components are typically 30-40 dB greater than the blood flow components. Therefore, it is desirable to reduce or eliminate the stationary signal components in order to detect blood flow accurately.

Generally, the wall-filtered complex I-Q signal is used to derive the Doppler shift frequency because the Doppler shift frequency and the blood velocity have the following relationship $$\Delta f = \frac{2 f_t v \cos\theta}{c} \quad (1)$$

where $\Delta f$ is the Doppler shift frequency, $f_t$ is the transmitted frequency, v is the blood velocity, $\theta$ is the angle between the ultrasound beam direction and the velocity vector and c is the speed of sound. The Doppler shift frequency is thus dependent on the angle between the velocity direction and the ultrasound beam direction and is a measurement that an ultrasound color Doppler system may obtain. Velocity (also called flow velocity, color velocity, color flow velocity, color Doppler velocity and others) derived from the Doppler shift frequency is usually the velocity component (i.e., v cos $\theta$) in the ultrasound beam direction or the projection of true flow velocity v onto to the ultrasound beam direction unless the angle is known or measured and corrected accordingly.

In the case of color Doppler, the number of the sampled signals is limited to only about 10. Therefore, an auto-correlation technique is usually used to determine the phase differences between the wall-filtered I-Q signal and then to determine the Doppler shift frequency and the blood flow velocity as follows. The color Doppler's I-Q signals $z(n)=x(n)+jy(n)$ are used to calculate "auto-correlation" R as shown in the following equation, where z(n) is the wall-filtered complex I-Q Doppler signal, x(n) is the in-phase (real) signal, y(n) is the quadrature phase (imaginary) signal, n indicates the signal number, j is the imaginary unit and * indicates the complex conjugate.

$$R = \tau z(n) \cdot z^*(n-1) \quad (2)$$

The real (Real(R)) and imaginary (Imag (R)) parts of R are used to obtain the phase $\phi$ as shown in the following equation.

$$\varphi = \tan^{-1} \frac{\text{Imag}(R)}{\text{Real}(R)} \quad (3)$$

Since $\tan^{-1}$ usually provides only $-0.5\pi$ to $0.5\pi$, the position of complex value R in the complex coordinate may be also used to derive $\phi$ in the range of $-\pi$ to $\pi$. The phase (i.e., color Doppler phase) $\phi$ is then related to the Doppler shift frequency as shown in the following equation.

$$\Delta f = \frac{\varphi f_{PRF}}{2\pi} \quad (4)$$

As shown in equation 4, a color Doppler phase of $2\pi$ corresponds to a Doppler shift frequency of the pulse repetition frequency $f_{PRF}$. Or a color Doppler phase of $\pi$ corresponds to a Doppler shift frequency of $$\frac{1}{2} f_{PRF}$$

while a color Doppler phase of $-\pi$ corresponds to a Doppler shift frequency of $$-\frac{1}{2} f_{PRF}.$$

A flow velocity (color flow velocity) in the positive direction corresponds to a positive Doppler shift frequency and a positive color Doppler phase while a flow velocity (color flow velocity) in the negative direction corresponds to a negative Doppler shift frequency and a negative color Doppler phase.

Other techniques can be used to obtain the phase and the Doppler shift frequency and the blood flow velocity. The Doppler shift frequency indicates the blood flow velocity. Additionally, the power of the high-pass filtered Doppler I-Q signals indicates the existence of blood flow and the variance of the data indicates turbulence.

Because the color Doppler signals are obtained by the pulsed ultrasound (and also sampling) technique, sampling theory dictates a maximum frequency limit. The maximum frequency is generally half of the pulse repetition frequency (PRF) or $f_{PRF}$. Since the autocorrelation is performed on the complex I-Q Doppler signals, blood flow velocity in a negative direction appears in the negative frequency domain. Therefore, the color Doppler velocity has negative frequencies that correspond to negative velocities. Thus, the Doppler shift frequency usually has a range of $$-\frac{f_{PRF}}{2} \text{ to } \frac{f_{PRF}}{2}$$

in frequency and the corresponding maximum velocities.

Some embodiments employ other Doppler shift frequency ranges. For example, the range may incorporate a "baseline shift" in which the center frequency of the range is not equal to zero. In some embodiments, the baseline shift may be selected from a range of frequencies between $$-\frac{f_{PRF}}{2} \text{ and } \frac{f_{PRF}}{2}.$$

In a particular example as shown in FIG. 11C, a Doppler shift frequency range of $$-\frac{f_{PRF}}{4} \text{ to } \frac{3f_{PRF}}{4}$$

reflects a baseline shift of $$-\frac{f_{PRF}}{4}.$$

This Doppler frequency range is associated with a negative maximum velocity corresponding to $$-\frac{f_{PRF}}{4}$$

and a positive maximum velocity corresponding to $$\frac{3f_{PRF}}{4}.$$

Similarly, a Doppler shift frequency range of $$-\frac{3f_{PRF}}{4} \text{ to } \frac{f_{PRF}}{4}$$

reflects a baseline shift of $$\frac{f_{PRF}}{4}$$

as shown in FIG. 11B. This Doppler frequency range is associated with a negative maximum velocity corresponding to $$-\frac{3f_{PRF}}{4}$$

and a positive maximum velocity corresponding to $$\frac{f_{PRF}}{4}.$$

FIG. 11A corresponds to the Doppler shift frequency ranges of FIG. 1B and FIG. 2B, in which the baseline (i.e., 0 Hz) is in the center of the Doppler shift frequency (velocity) scale. When the baseline is shifted, e.g. by $$\frac{f_{PRF}}{4}$$

as shown in FIG. 11B, the positive maximum frequency becomes $$\frac{f_{PRF}}{4}$$

while the negative maximum frequency becomes $$-\frac{3f_{PRF}}{4}.$$

If the baseline shift is $$-\frac{f_{PRF}}{4},$$

the positive maximum frequency becomes $$\frac{3f_{PRF}}{4}$$

while the negative maximum frequency decreases to $$-\frac{f_{PRF}}{4}$$

as shown in FIG. 11C. In other words, the positive maximum frequency is decreased by the baseline shift while the absolute magnitude of the negative maximum frequency is increased by the baseline shift.

Often in cardiovascular applications, blood velocities may exceed these maximum velocities, resulting in aliasing. Color Doppler imaging uses color coding methods to display blood velocities (or Doppler shift frequencies) in colors. For example, the positive velocities may be displayed in shades of red, i.e. higher velocities are shown with lighter red and lower velocities are shown with darker red, while the negative velocities may be displayed in shades of blue, i.e. higher velocities are shown with lighter blue and lower velocities are shown with darker blue. Other color coding methods can be used to represent blood flow velocities. When aliasing occurs, the color flow image may wrap around at the positive maximum frequency, with frequencies exceeding the maximum limit appearing in the negative frequencies coded colors, or wrap around at the negative maximum frequency, with frequencies exceeding the negative maximum limit appearing in the positive frequencies coded colors. Aliasing therefore complicates the blood velocity image and makes any diagnosis based thereon difficult.

A color Doppler flow image of correct length dimensions is created by scan-converting color Doppler flow lines which in turn are created by processing color Doppler I-Q data. Scan conversion is based on the type of probe and image format used, i.e. sector, convex or linear scan formats. Color Doppler flow lines represent flow velocities detected along the ultrasound beams transmitted and received and contain the smaller number of data than the scan-converted color flow image. Therefore, in some embodiments, color Doppler flow lines are used for faster processing.

Figure 2:
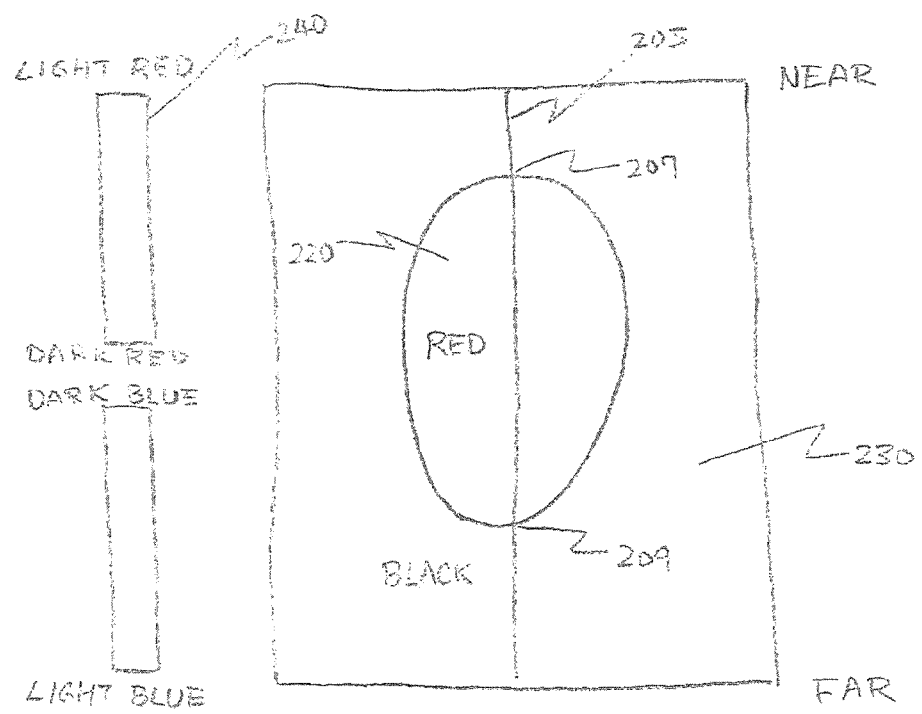
FIG. 2: Non-aliased color Doppler flow line data.

FIG. 2 represents, for example, 100 color Doppler flow lines before scan-conversion, although only one flow line 205 is distinctively shown. The top portion of the image represents a field closer to the ultrasound probe and is generally called a near field. The bottom portion of the image is called a far field and represents a field farthest from the ultrasound probe. FIG. 2 includes a color flow area 220 (red) in the middle of the color flow lines surrounded by black areas 230, which represent flow velocities of zero.

To the left of the color flow lines, a color coding 240 is shown to associate flow velocities with representative colors. The positive (flow toward the ultrasound probe) maximum velocity, which usually corresponds to half the pulse repetition frequency (PRF), is represented by light red and the positive minimum detectable velocity is represented by dark red. Positive velocities between these extreme values are represented by intermediate shades of red. The negative maximum velocity, which usually corresponds to –(0.5 PRF), is represented by light blue and the negative minimum detectable velocity is represented by dark blue. Negative velocities between these extreme values are represented by intermediate shades of blue. Zero flow velocity is coded black. Other color coding schemes may be employed.

If we follow the flow line 205 from the top (near field) to the bottom (far field), we encounter two transitions, black-red transition 207 and red-black transition 209. A transition is defined as a point at which flow direction changes (e.g., from positive to negative, from negative to positive, from negative to zero, from positive to zero, from zero to negative, or from zero to positive). Since the black portion of the flow line 205 immediately adjacent to the transition 207 represents a flow of zero velocity, the velocity represented by the red portion of the flow line 205 immediately adjacent to the transition 207 is considered correct and non-aliased. Since the red color at the transition 207 is considered non-aliased, velocities of the following area (or points) along the flow line 205 until the next transition are all considered correct and non-aliased.

At the next red-black transition 209, the color changes from red to black (zero velocity). By definition, black area 230 on the far side of transition 209 shows no aliasing. This procedure is performed along every flow line to detect aliasing in FIG. 2. Since there are no aliased areas along any flow line in the case of FIG. 2, no correction is necessary.

FIG. 1 represents, for example, 100 color Doppler flow lines before scan-conversion, although only one flow line 105 is distinctively shown. Areas showing an overall reddish color indicate flow toward the probe while areas showing an overall bluish color indicate flow away from the probe.

Color flow areas in the middle of the flow lines are either a shade of blue 130 or red 120. The center area 130 is coded shades of blue surrounded by an area 120 of shades of red, which is in turn surrounded by black areas 140. If we follow the color flow line 105 from the near field to far field, we will detect areas of black, red, blue, red and black in that order. This progression represents four transitions, i.e. black-red transition 107, red-blue transition 109, blue-red transition 111 and red-black transition 113.

Initially, the red color at the far side of black-red transition 107 may be considered a true color or non-aliased in this flow condition because it is preceded along flow line 105 by black (zero velocity) area 140. Therefore, the flow velocities are not aliased on the flow line 105 from the black-red transition 107 to red-blue transition 109. Red-blue transition 109 represents a transition between opposite flow directions. Accordingly, the absolute velocity difference across the transition is calculated, i.e. a velocity represented by the red color at transition 109 minus a velocity represented by the blue color at transition 109. If the absolute velocity difference is greater than the velocity corresponding to half the pulse repetition frequency (PRF) or another preset value, the velocity represented by the blue color is considered aliased. Once the blue color at the transition is considered aliased, velocities represented by the following continuous shades of blue area (or points) are considered aliased until blue-red transition 111.

Aliasing stops at blue-red transition 111. Therefore, the velocities represented by shades of red from transition 111 to transition 113 are considered non-aliased. Again, black area 140 on the far side of transition 113, by definition, shows no aliasing. If a next color representing a non-zero flow velocity (i.e., either positive or negative) was identified along flow line 105 after black area 140, the next color would become the reference color or the reference direction representing a true (i.e., non-aliased) velocity.

Figure 10:
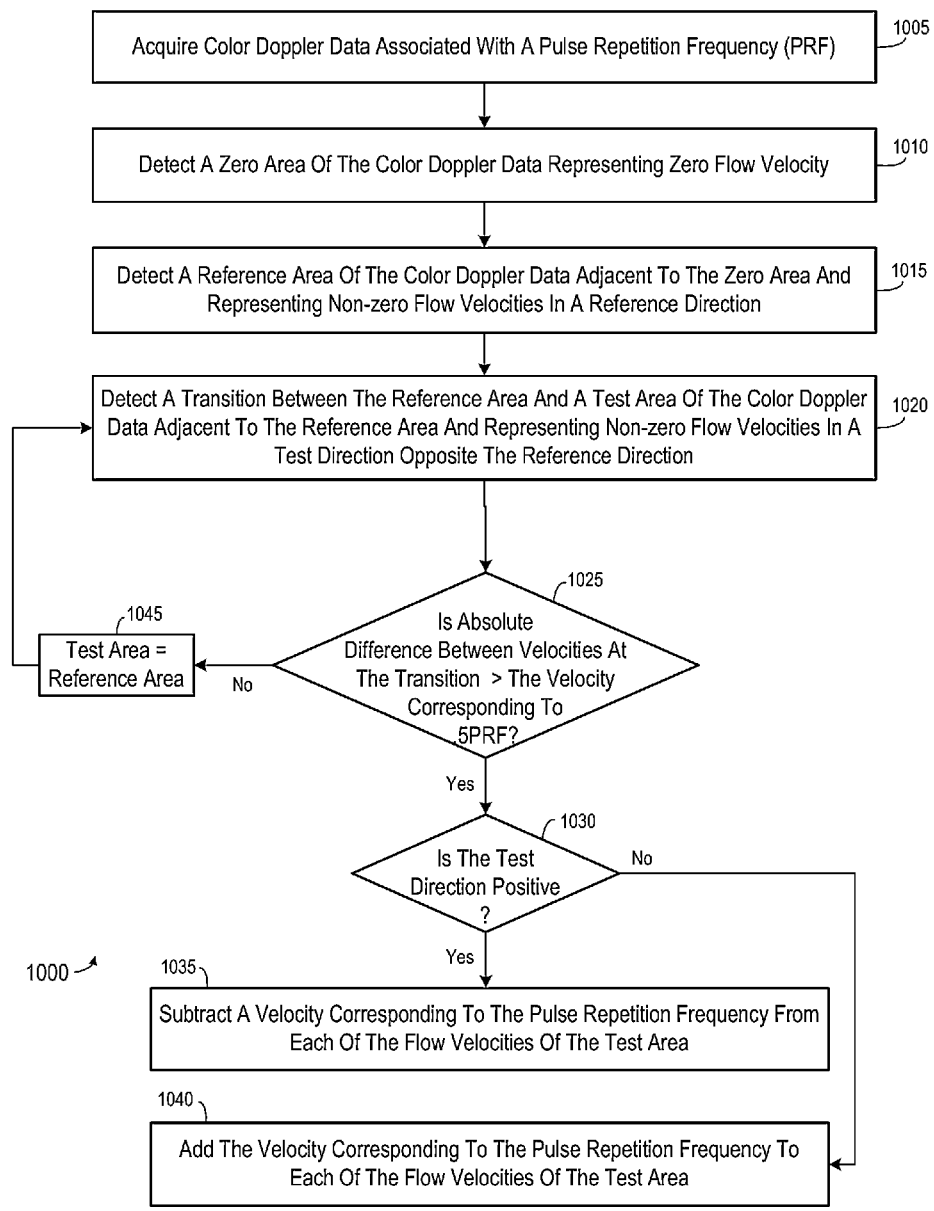
FIG. 10: A flow diagram of a process to address aliasing according to some embodiments.

FIG. 10 illustrates a flow diagram of process 1000 to detect and correct aliasing within color Doppler data according to some embodiments. Process 1000 may be embodied in any combination of hardware and/or software. In one example, process 1000 is embodied in processor-executable process steps stored on a tangible medium. Process 1000 may be executed by a correction unit as will be described below with respect to FIGS. 4 and 5.

Initially, at 1005, color Doppler data associated with a pulse repetition frequency is acquired. As described above, the acquired color Doppler data may be generated based on sampled data as shown in equation 2. The frequency of these samples is equal to the pulse repetition frequency.

As used herein, "color Doppler data" may refer to color flow line data or color Doppler image data (i.e., scan-converted image data) generated from such color flow line data. Accordingly, process 1000 may be performed on either type of Doppler data.

Next, at 1010, a "zero" area of the color Doppler data is detected. A zero area is an area of the color Doppler data which represents a zero flow velocity. With respect to the example of FIG. 1, the "near" area 140 of the color Doppler data appears black and therefore represent zero flow velocity.

A reference area of the color Doppler data adjacent to the zero area is detected at 1015. The reference area is an area of the color Doppler data which represents non-zero flow velocities in a single direction, which will be initially referred to as the reference direction. The foregoing processing assumes that the flow velocities of the reference area are non-aliased because the reference area is adjacent to the zero area and a flow velocity may not change rapidly.

For purposes of the present example, it will be assumed that the area detection of process 1000 proceeds along flow line 105 of FIG. 1. Accordingly, area 120 is initially detected at 1015. Then, at 1020, a transition between the reference area and a test area of the color Doppler data adjacent to the reference area is detected. The test area is an area of the color Doppler data which represents non-zero flow velocities in a "test" direction opposite to the reference direction.

Continuing with the present example, transition 109 is detected at 1020. As shown in FIG. 1, transition 109 is between the reference area 120 and test area 130, which represents non-zero flow velocities in a test direction (i.e., represented by blue shades) opposite to the reference direction (i.e., represented by red shades).

At 1025, it is determined whether the absolute difference between flow velocities at the detected transition is greater than the flow velocity associated with one half of the pulse repetition frequency or another preset value. For example, a velocity represented by a blue color at transition 109 is subtracted from a velocity represented by a red color at transition 109. If the absolute magnitude of the result is greater than the velocity corresponding to one half of the pulse repetition frequency (PRF) or another preset value, the velocity represented by the blue color is considered aliased.

Assuming that the determination at 1025 is affirmative, flow continues to 1030 to determine whether the current test direction is positive. This determination is used to determine how to correct the aliased test area. If the test direction is positive (i.e., toward the ultrasound transducer), a velocity corresponding to the pulse repetition frequency is subtracted from each of the flow velocities of the test area along color flow line 105 at 1035. If the test direction is negative (i.e., away from the ultrasound transducer), a velocity corresponding to the pulse repetition frequency is added to each of the flow velocities of the test area along color flow line 105 at 1040.

If the determination at 1025 is negative, the current test area is denoted as the reference area (i.e., because the current test area was either determined to be non-aliased at 1025), and flow returns to 1020 to continue as described above, with a lower part of area 120 becoming the next test area at 1020. In other words, the reference, true flow direction and color may be reset multiple times in a color flow line.

When we follow a color flow line, we may encounter a black area with zero velocities after observing either shades of red or blue in the middle of flow field. A next color area of either shades of red or blue adjacent to the black area may be considered a true color area with correct velocities without aliasing and registered as a reference flow direction (or color).

Thereafter, the foregoing procedure in the previous paragraphs may be performed using the newly defined true flow direction at this point. In other words, the reference, true flow direction and color may be reset multiple times in a color flow line.

Although only one color flow line is considered in the above example, process 1000 may be repeated for any number of color flow lines.

The process 1000 operates based on velocity values (i.e., color velocity, color Doppler velocity, color flow velocity, v cos θ), however, the process 1000 may also operate based on Doppler shift frequency values or color Doppler phase values as shown in equation (1), (3) and (4). Velocity values, Doppler shift frequency values and color Doppler phase values may be collectively referred to as color Doppler values.

Color Doppler data may contain noise. Therefore, pre-processing may be performed before the above-mentioned aliasing detection and correction procedure. In addition, post-processing may be performed after the above-mentioned aliasing detection and correction procedure. The pre-processing or post-processing may be selected from low-pass filtering, band-pass filtering, high-pass filtering, median filter, mode, mean or others of either one-dimensional, two-dimensional, three-dimensional or four-dimensional (i.e. three-dimension plus temporal).

Figure 6B:
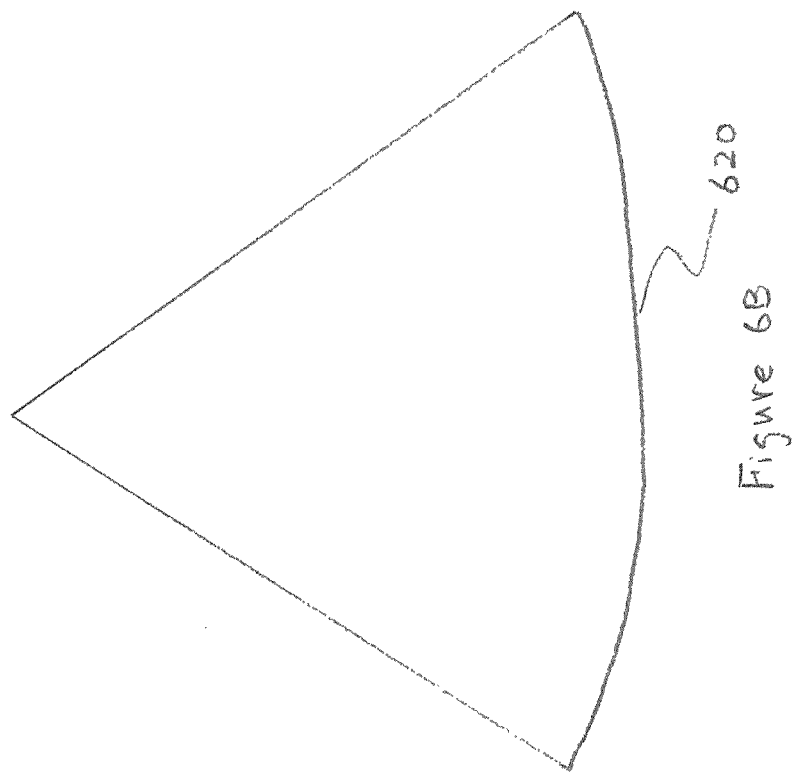
FIG. 6B: A representation of a scan-converted color flow image.
Figure 6A:
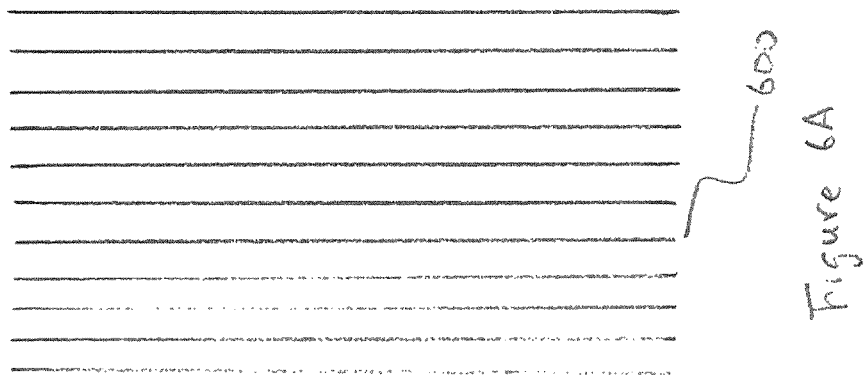
FIG. 6A: A representation of color flow lines.
Figure 7B:
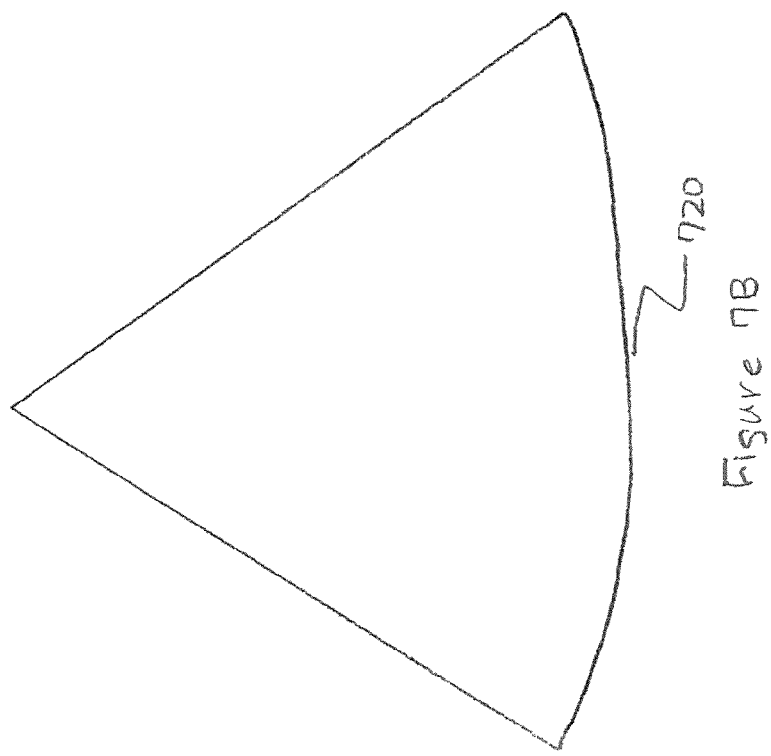
FIG. 7B: A representation of a scan-converted B-mode image.
Figure 7A:
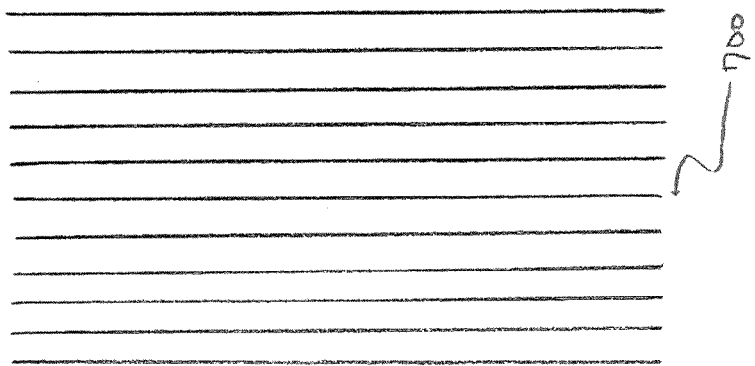
FIG. 7A: A representation of B-mode lines.

As mentioned above, process 1000 may be applied to color flow line data or color Doppler image data according to some embodiments. FIG. 6A shows color flow lines 600 before scan-conversion, although only 11 lines are shown as an example. A color flow line consists of many color flow data samples along the line. Color flow lines are created from color beam data and may not show correct spatial dimensions. Scan-conversion is a technique to convert the color flow lines to a raster video image by interpolating the color flow lines. In a scan-converted image (e.g., sector scan) shown FIG. 6B, the color flow image consists of color flow image pixels of the orthogonal (x-y) coordinate with the correct length relationship (vertical vs. horizontal dimensions) in contrast to the color flow lines shown in FIG. 6A. B-mode imaging also uses the scan-conversion technique to convert B-mode lines as shown in FIG. 7A to a B-mode image as shown in FIG. 7B by interpolating B-mode line data.

Process 1000 may begin at a near or far field in some embodiments. Alternately, process 1000 may be performed from both near and far fields.

Embodiments of process 1000 may operate upon color flow lines 800 by one line at a time as shown in FIG. 8A, where color flow data samples are represented by dots 820. More specifically, process 1000 may proceed from one end of a color flow line to another end and then onto the next color flow line until the last color flow line is processed. A color flow line 800 represents many color flow data samples 820 in a color flow beam.

In some embodiments, process 1000 is performed horizontally across color flow lines 840 as shown in FIG. 8B, using color flow line data samples 830. Process 1000 may be performed diagonally across color flow lines 860 as shown in FIG. 8C, using the color flow line data samples 850.

Figure 9C:
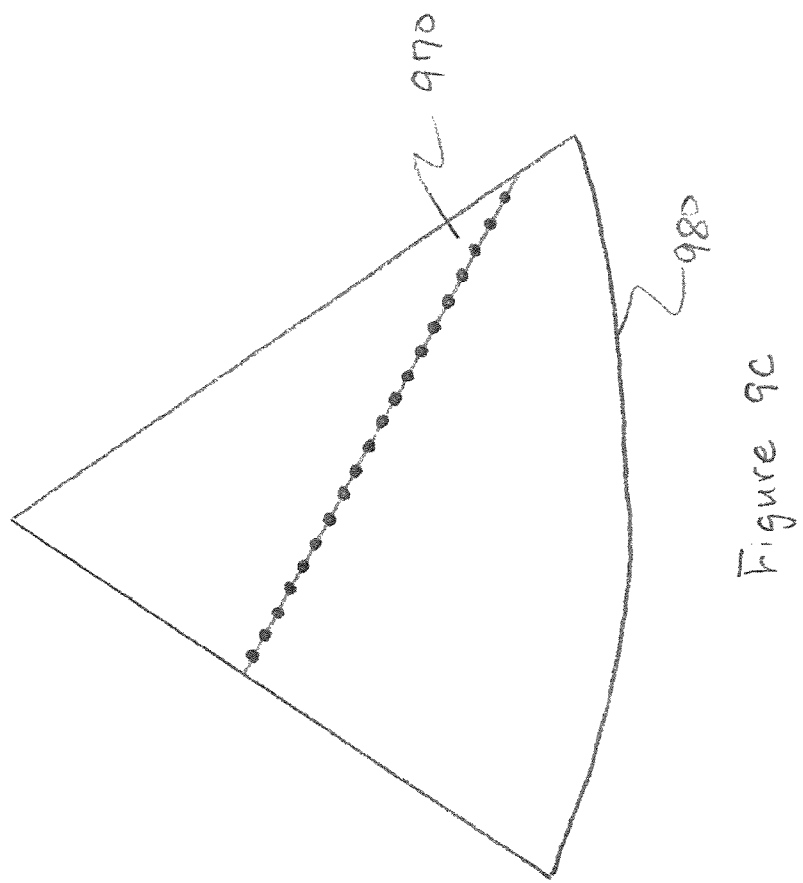
FIG. 9C: Aliasing detection in a diagonal direction using a color flow image.

Process 1000, in some embodiments, is performed on a scan-converted color flow image 620 pixel by pixel. The color flow image 620 is obtained by scan-converting the color flow lines 600. In some embodiments, as shown in FIG. 9A using color flow data samples 920, process 1000 is performed vertically from top to bottom in a first color flow image column and moves onto the next column until the last column is reached. Alternately, as shown in FIG. 9B using color flow data samples 940, process 1000 may be performed horizontally. As shown in FIG. 9C, using color flow data samples 970, process 1000 may be performed diagonally across a color flow image 980. The path traversed by a process according to some embodiments may be a straight line or a curve.

To find the vessel or cardiac boundary (i.e., a first area representing zero flow velocity), a scan-converted B-mode image 720 may be used. Alternately, B-mode line data 700 may be used. In an alternate embodiment, the B-mode image 720 may not be used to find the vessel or cardiac boundary. Instead, color flow data 600 or 620 itself is used to find the boundary. On the boundary, the blood flow velocity is zero and thus is assigned the color black (or no color). The color flow velocity may be also used to find the boundary. The power of color flow data before and/or after the wall-filtering may also be used to find the boundary. The power of color flow data before the wall-filtering may be similar to the B-mode signal while the power of color flow data after the wall-filtering indicates flow.

Figure 3:
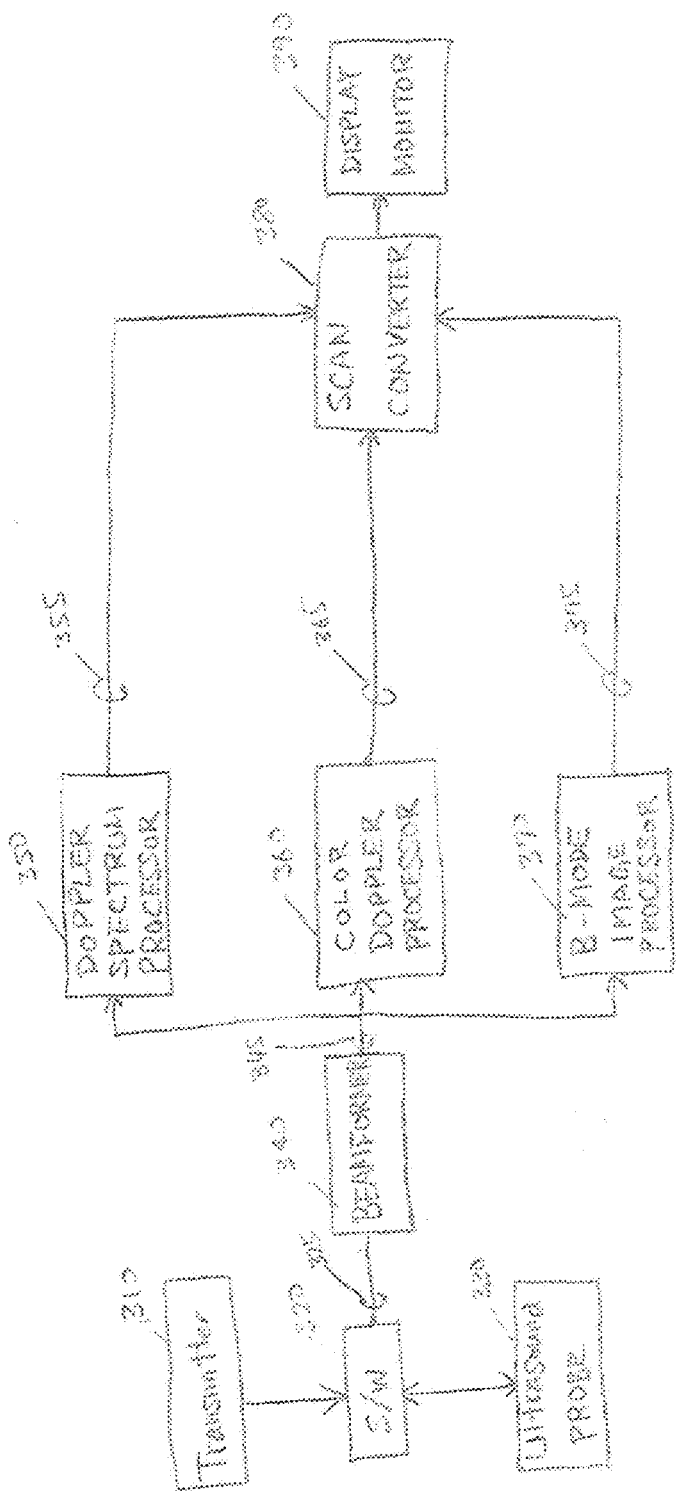
FIG. 3: A diagram of an ultrasound diagnostic imaging system (prior art).

FIG. 3 shows a diagram of a conventional ultrasound diagnostic imaging system with B-mode imaging, Doppler spectrum and color Doppler imaging (e.g., see U.S. Pat. No. 4,573,477, U.S. Pat. No. 4,622,977, U.S. Pat. No. 4,641,668, U.S. Pat. No. 4,651,742, U.S. Pat. No. 4,651,745, U.S. Pat. No. 4,759,375, U.S. Pat. No. 4,766,905, U.S. Pat. No. 4,768,515, U.S. Pat. No. 4,771,789, U.S. Pat. No. 4,780,837, U.S. Pat. No. 4,799,490, and U.S. Pat. No. 4,961,427). The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter 310 through a transmit/receive switch 320. The probe 320 may consist of an array of transducer elements which are separately driven by the transmitter with different time-delays so that a transmit ultrasound beam is focused and steered. A beamformer 340 receives the received ultrasound signal(s) from the probe 330 through the switch 320 and processes the signal(s) 325. The beamformer applies delays and/or phases to the signals and the resultant signals are summed for focusing and steering a receive ultrasound beam. The beamformer may also apply apodization, amplification and filtering.

The processed signal 345 is coupled to a Doppler spectrum processor 350, a color flow processor 360, and a B-mode image processor 370. The Doppler spectrum processor 350 includes a Doppler signal processor and a spectrum analyzer, and processes Doppler flow velocity signals and calculates and outputs a Doppler spectrum 355. The color flow processor 360 processes the received signal 345 and calculates and outputs velocity, power and variance signals 365. The B-mode image processor 370 processes the received signal 345 and calculates and outputs a B-mode image 375 or the amplitude of the signal by an amplitude detection.

The Doppler spectrum signals 355, color flow processor signals (velocity, power, and variance) 365 and B-mode processor signals 375 are coupled to a scan converter 380 that converts the signals to scan-converted signals. The output of scan converter 380 is coupled to a display monitor 390 for displaying ultrasound images.

The color Doppler processor has a range of $$-\frac{f_{PRF}}{2} \text{ to } \frac{f_{PRF}}{2}$$

for the Doppler shift frequency as a default setting but the range may be unequally allocated to the positive frequency and the negative frequency as the "zero-velocity" baseline shift may be performed. For example, a range of $$-\frac{f_{PRF}}{4} \text{ to } \frac{3f_{PRF}}{4}$$

may be set with a baseline shift of $$\frac{f_{PRF}}{4}.$$

Figure 4:
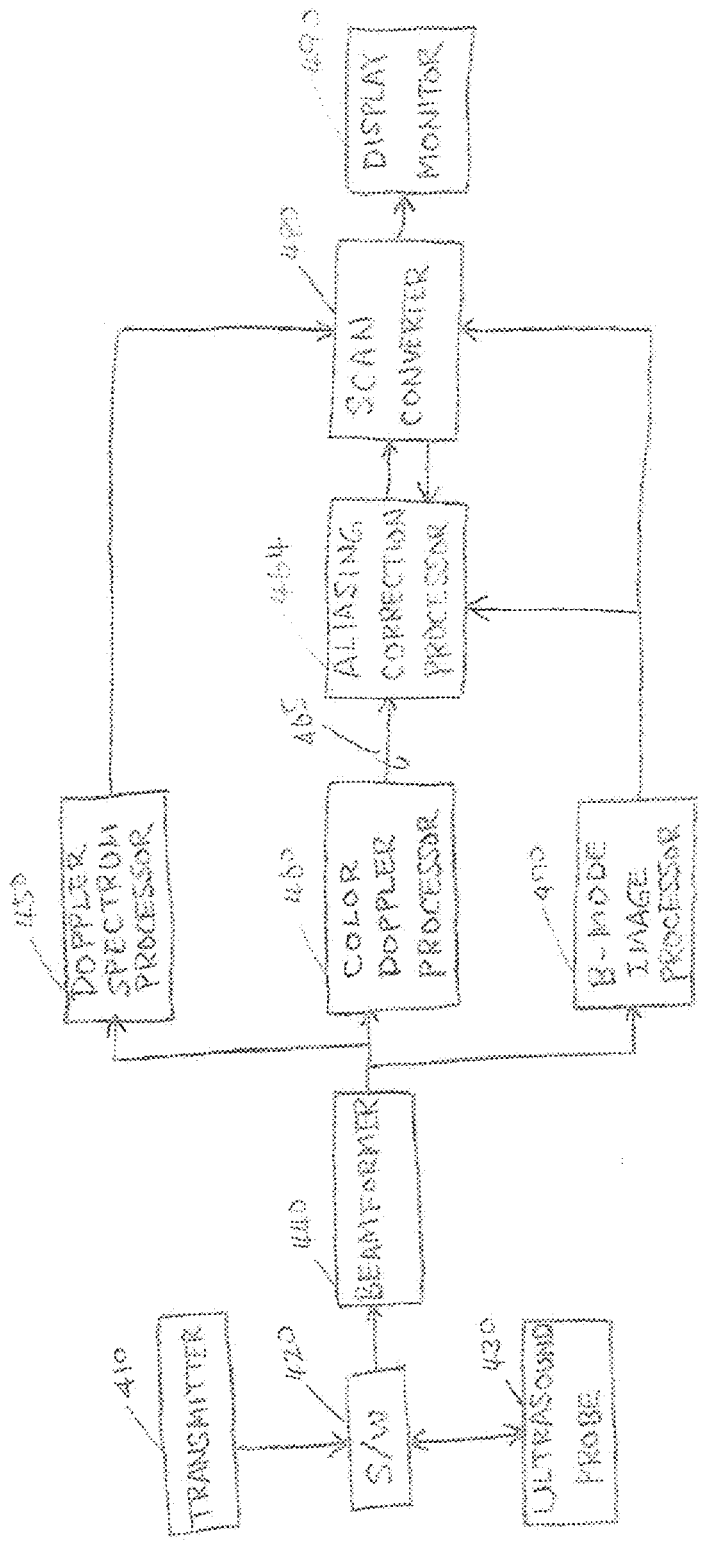
FIG. 4: A diagram of an ultrasound diagnostic imaging system according to some embodiments and using line data.

FIG. 4 shows a diagram of an ultrasound imaging system including a color Doppler aliasing correction processor 464 according to some embodiments. The aliasing correction processor 464 receives output 465 from the color Doppler processor 460 as well as the scan-converted B-mode image from the scan converter 480. The scan-converted B-mode image may be used to provide information. Color Doppler data in this case are line data rather than the scan-converted color Doppler image. The aliasing correction receives the scan-converted B-mode image and finds color Doppler image pixels corresponding to the B-mode image. Alternately, the B-mode image processor's output may be directly input to the aliasing correction processor to provide information. As discussed previously, color Doppler data are tested and corrected for aliasing in the line data domain rather than the scan-converted color Doppler image in this case.

Figure 5:
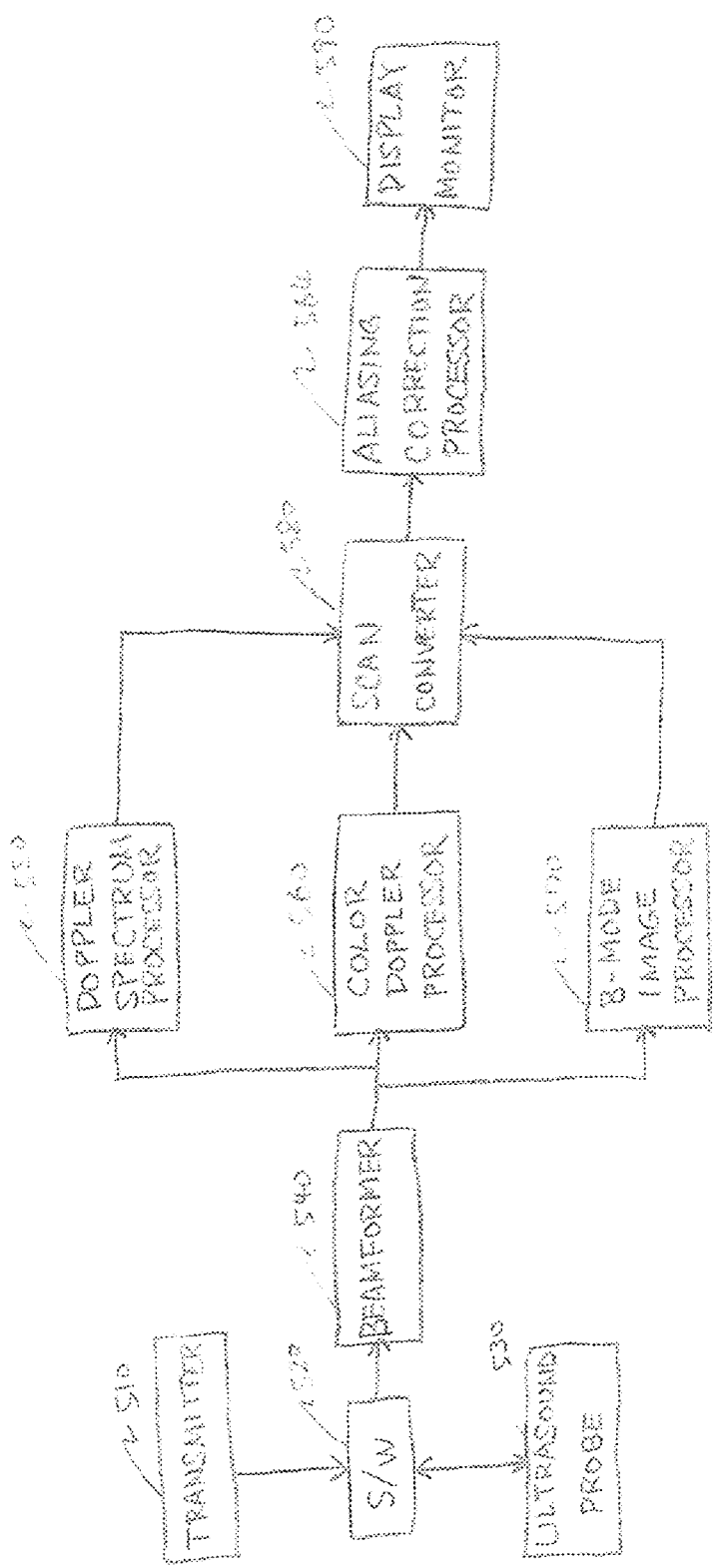
FIG. 5: A diagram of an ultrasound diagnostic imaging system according to some embodiments and using scan-converted images.

FIG. 5 shows a diagram of embodiments in which the test and correction of color Doppler aliasing is performed in the scan-converted image domain rather than the line data domain which was discussed previously. The B-mode image and color Doppler image are all scan-converted before the aliasing correction processor performs the processing.

The aliasing correction processors 464, 564 may be comprised of general purpose central processing units (CPUs), digital signal processors (DSPs), field programmable Arrays (FPGAs), graphic processing units (GPUs) and/or discreet electronic devices.

The foregoing description references velocity, velocity aliasing and velocity aliasing corrections. However, the description may be equally applicable to the frequency domain or the phase domain via equations (1), (3) and (4). The velocity or color velocity, which is actually the velocity component v cos θ in the ultrasound beam direction as shown in equation (1), may be converted to the Doppler shift frequency via equation (1). Then, the Doppler shift frequency in turn may be converted to a phase or the color Doppler phase via equation (4). Velocity aliasing may be converted to frequency aliasing or phase aliasing. Aliasing correction may be applied to Doppler shift frequency values in the frequency domain or color Doppler phase values in the phase domain.

Color velocity, color flow velocity, color Doppler velocity, flow velocity or velocity discussed herein are directly related to the Doppler shift frequency via equation (1) and are actually the flow velocity component in the ultrasound beam direction as implied by cos θ or the projection of the true flow velocity onto the ultrasound beam direction assuming no aliasing.

The positive velocity or positive velocity direction refers to a flow that is directed toward the ultrasound transducer within a range of +/−90 degrees from the center axis of the ultrasound beam rather than away from the transducer. The negative velocity or negative velocity direction refers to flow directed away from the ultrasound transducer with a range of +/−90 degrees from the center axis of ultrasound beam.

One or more embodiments have been described. Nevertheless, various modifications will be apparent to those in the art.

What is claimed is:

1. A method comprising:
acquiring color Doppler data associated with a pulse repetition frequency ($f_{PRF}$);
detecting a first area of the color Doppler data representing a zero color Doppler value;
detecting a second area of the color Doppler data adjacent to the first area and representing non-zero color Doppler values in a first direction;
detecting a first transition between the second area and a third area of the color Doppler data adjacent to the second area and representing non-zero color Doppler values in a second direction opposite the first direction;
determining whether the absolute difference between color Doppler values of the second area and the third area at the first transition is more than a preset value;

in response to a determination that the absolute difference between color Doppler values of the second area and the third area at the first transition is more than the preset value, subtracting a color Doppler value corresponding to a Doppler shift frequency of $f_{PRF}$ from each of the color Doppler values of the third area if the second direction is positive; and in response to the determination that the absolute difference between color Doppler values of the second area and the third area at the first transition is more than the preset value, adding the color Doppler values corresponding to a Doppler shift frequency of $f_{PRF}$ to each of the color Doppler values of the third area if the second direction is negative.

2. A method according to claim 1, wherein the color Doppler data comprises color flow line data.

3. A method according to claim 1, wherein the color Doppler data comprises scan-converted color flow image data.

4. A method according to claim 1, wherein detecting the first area of the color Doppler data representing a zero color Doppler value comprises:
  detecting the first area of the color Doppler data based on B-mode data or the color Doppler data.

5. A method according to claim 1, wherein detecting the second area and the first transition may proceed along a color flow line, a line across color flow lines, a vertical or horizontal line in a scan-converted color flow image, or a line across said scan-converted image columns.

6. A method according to claim 1, wherein said preset value is a color Doppler value corresponding to a Doppler shift frequency of half the pulse repetition frequency.

7. A method according to claim 1, wherein determining whether the absolute difference between color Doppler values of the second area and the third area at the first transition is more than the preset value comprises determining that that the absolute difference between color Doppler values of the second area and the third area at the first transition is not more than the preset value, the method further comprising:
  detecting a fourth area of the color Doppler data adjacent to the third area and representing non-zero color Doppler values in the first direction;
  detecting a second transition between the third area and the fourth area;
  determining that the absolute difference between color Doppler values of the third area and the fourth area at the second transition is more than the preset value;
  in response to the determination that the absolute difference between color Doppler values of the third area and the fourth area at the second transition is more than the preset value, subtracting a color Doppler value corresponding to a Doppler shift frequency of $f_{PRF}$ from each of the color Doppler values of the fourth area if the first direction is positive; and
  in response to the determination that the absolute difference between color Doppler values of the third area and the fourth area at the second transition is more than the preset value, adding the color Doppler value corresponding to a Doppler shift frequency of $f_{PRF}$ to each of the color Doppler values of the fourth area if the first direction is negative.

8. A method according to claim 1, further comprising:
  detecting a fourth area of the color Doppler data representing a zero color Doppler value;
  detecting a fifth area of the color Doppler data adjacent to the fourth area and representing non-zero color Doppler values in a third direction, wherein the third direction may be equivalent to the first direction or to the second direction;
  detecting a first transition between the fifth area and a sixth area of the color Doppler data adjacent to the fifth area and representing non-zero color Doppler values in a fourth direction opposite the third direction;
  determining that the absolute difference between color Doppler values of the fifth area and the sixth area at the second transition is more than a preset value;
  in response to the determination that the absolute difference between color Doppler values of the fifth area and the sixth area at the second transition is more than the preset value, subtracting a color Doppler value corresponding to a Doppler shift frequency of $f_{PRF}$ from each of the color Doppler values of the sixth area if the fourth direction is positive; and
  in response to the determination that the absolute difference between color Doppler values of the fifth area and the sixth area at the second transition is more than the preset value, adding the color Doppler values corresponding to a Doppler shift frequency of $f_{PRF}$ to each of the color Doppler values of the sixth area if the fourth direction is negative.

9. A method according to claim 1, wherein said color Doppler values comprise color flow velocities, Doppler shift frequencies or color Doppler phases.

10. A system comprising:
  an aliasing correction processor to:
    acquire color Doppler data associated with a pulse repetition frequency ($f_{PRF}$);
    detect a first area of the color Doppler data representing a zero color Doppler value;
    detect a second area of the color Doppler data adjacent to the first area and representing non-zero color Doppler values in a first direction;
    detect a first transition between the second area and a third area of the color Doppler data adjacent to the second area and representing non-zero color Doppler values in a second direction opposite the first direction;
    determine whether the absolute difference between color Doppler values of the second area and the third area at the first transition is more than a preset value;
    in response to a determination that the absolute difference between color Doppler values of the second area and the third area at the first transition is more than the preset value, subtracting a color Doppler value corresponding to a Doppler shift frequency of $f_{PRF}$ from each of the color Doppler values of the third area if the second direction is positive; and
    in response to the determination that the absolute difference between color Doppler values of the second area and the third area at the first transition is more than the preset value, adding the color Doppler value corresponding to a Doppler shift frequency of $f_{PRF}$ to each of the color Doppler value of the third area if the second direction is negative.

11. A system according to claim 10, further comprising a color Doppler processor to provide the color Doppler data to the aliasing correction processor,
  wherein the color Doppler data comprises color flow line data.

12. A system according to claim 10, further comprising a scan converter to provide the color Doppler data to the aliasing correction processor, wherein the color Doppler data comprises scan-converted color flow image data.

13. A system according to claim 10, wherein detecting the first area of the color Doppler data representing zero color Doppler value comprises:
    detecting the first area of the color Doppler data based on B-mode data or the color Doppler data.

14. A system according to claim 10, wherein detecting the second area and the first transition may proceed along a color flow line, a line across color flow lines, a vertical or horizontal line in a scan-converted color flow image, or a line across said scan-converted image columns.

15. A system according to claim 10, wherein said preset value is a color Doppler value corresponding to a Doppler shift frequency of half the pulse repetition frequency.

16. A system according to claim 10, wherein the determination of whether the absolute difference between color Doppler values of the second area and the third area at the first transition is more than a preset value comprises a determination that the absolute difference between color Doppler values of the second area and the third area at the first transition is not more than the preset value, the processor further to:
    detect a fourth area of the color Doppler data adjacent to the third area and representing non-zero color Doppler values in the first direction;
    detect a second transition between the third area and the fourth area;
    determine that the absolute difference between color Doppler values of the third area and the fourth area at the second transition is more than the preset value;
    in response to the determination that the absolute difference between color Doppler values of the third area and the fourth area at the second transition is more than the preset value, subtract a color Doppler value corresponding to $f_{PRF}$ from each of the color Doppler value of the fourth area if the first direction is positive; and
    in response to the determination that the absolute difference between color Doppler values of the third area and the fourth area at the second transition is more than the preset value, add the color Doppler value corresponding to $f_{PRF}$ to each of the color Doppler values of the fourth area if the first direction is negative.

17. A system according to claim 10, the processor further to:
    detect a fourth area of the color Doppler data representing a zero color Doppler value;
    detect a fifth area of the color Doppler data adjacent to the fourth area and representing non-zero color Doppler values in a third direction, wherein the third direction may be equivalent to the first direction or to the second direction;
    detect a first transition between the fifth area and a sixth area of the color Doppler data adjacent to the fifth area and representing non-zero color Doppler values in a fourth direction opposite the third direction;
    determine that the absolute difference between color Doppler values of the fifth area and the sixth area at the second transition is more than the preset value;
    in response to the determination that the absolute difference between color Doppler values of the fifth area and the sixth area at the second transition is more than the preset value, subtract a color Doppler value corresponding to a Doppler shift frequency of $f_{PRF}$ from each of the color Doppler values of the sixth area if the fourth direction is positive; and
    in response to the determination that the absolute difference between color Doppler values of the fifth area and the sixth area at the second transition is more than the preset value, add the color Doppler values corresponding to a Doppler shift frequency of $f_{PRF}$ to each of the color Doppler values of the sixth area if the fourth direction is negative.

18. A tangible non-transitory computer-readable medium storing processor-executable program code, the program code comprising:
    code to acquire color Doppler data associated with a pulse repetition frequency ($f_{PRF}$);
    code to detect a first area of the color Doppler data representing a zero color Doppler value;
    code to detect a second area of the color Doppler data adjacent to the first area and representing non-zero color Doppler values in a first direction;
    code to detect a first transition between the second area and a third area of the color Doppler data adjacent to the second area and representing non-zero color Doppler values in a second direction opposite the first direction;
    code to determine whether the absolute difference between color Doppler values of the second area and the third area at the first transition is more than a preset value;
    code to subtract, in response to a determination that the absolute difference between color Doppler values of the second area and the third area at the first transition is more than the preset value, a color Doppler value corresponding to a Doppler shift frequency of $f_{PRF}$ from each of the color Doppler values of the third area if the second direction is positive; and
    code to add, in response to a determination that the absolute difference between color Doppler values of the second area and the third area at the first transition is more than the preset value, the color Doppler value corresponding to a Doppler shift frequency of $f_{PRF}$ to each of the color Doppler values of the third area if the second direction is negative.

19. A non-transitory medium according to claim 18, wherein the color Doppler data comprises color flow line data.

20. A non-transitory medium according to claim 18, wherein the color Doppler data comprises scan-converted color flow image data.

21. A non-transitory medium according to claim 18, wherein the code to detect the first image area of the color Doppler data representing zero color Doppler value comprises:
    code to detect the first area of the color Doppler data based on B-mode data or the color Doppler data.

22. A non-transitory medium according to claim 18, wherein detection of the second area and the first transition may proceed along a color flow line, a line across color flow lines, a vertical or horizontal line in a scan-converted color flow image, or a line across said scan-converted image columns.

23. A non-transitory medium according to claim 18, wherein said preset value is a color Doppler value corresponding to a Doppler shift frequency of half the pulse repetition frequency ($f_{PRF}$).

24. A non-transitory medium according to claim 18, wherein the determination of whether the absolute difference between color Doppler values of the second area and the third area at the first transition is more than a preset value comprises a determination that the absolute difference between color Doppler values of the second area and the third area at the first transition is not more than the preset value, the program code comprising code to:

detect a fourth area of the color Doppler data adjacent to the third area and representing non-zero color Doppler values in the first direction;

detect a second transition between the third area and the fourth area;

determine that the absolute difference between color Doppler values of the third area and the fourth area at the second transition is more than the preset value;

in response to the determination that the absolute difference between color Doppler values of the third area and the fourth area at the second transition is more than the preset value, subtract a color Doppler value corresponding to a Doppler shift frequency of $f_{PRF}$ from each of the color Doppler values of the fourth area if the first direction is positive; and in response to the determination that the absolute difference between color Doppler values of the third area and the fourth area at the second transition is more than the preset value, add the color Doppler value corresponding to a Doppler shift frequency of $f_{PRF}$ to each of the color Doppler values of the fourth area if the first direction is negative.

25. A non-transitory medium according to claim 18, the code further comprising:

code to detect a fourth area of the color Doppler data representing a zero color Doppler value;

code to detect a fifth area of the color Doppler data adjacent to the fourth area and representing non-zero color Doppler values in a third direction, wherein the third direction may be equivalent to the first direction or to the second direction;

code to detect a first transition between the fifth area and a sixth area of the color Doppler data adjacent to the fifth area and representing non-zero color Doppler values in a fourth direction opposite the third direction;

code to determine that the absolute difference between color Doppler values of the fifth area and the sixth area at the second transition is more than a preset value;

code to subtract, in response to the determination that the absolute difference between color Doppler values of the fifth area and the sixth area at the second transition is more than a preset value, a color Doppler value corresponding to a Doppler shift frequency of $f_{PRF}$ from each of the color Doppler values of the sixth area if the fourth direction is positive; and code to add, in response to the determination that the absolute difference between color Doppler values of the fifth area and the sixth area at the second transition is more than a preset value, the color Doppler values corresponding to a Doppler shift frequency of $f_{PRF}$ to each of the color Doppler values of the sixth area if the fourth direction is negative.

* * * * *